United States Patent
Fritz et al.

(10) Patent No.: US 6,255,531 B1
(45) Date of Patent: *Jul. 3, 2001

(54) BORON COMPOUNDS AND OTHER COMPOUNDS OF GROUP IIIA

(75) Inventors: Cornelia Fritz, Frankfurt; Frank Küber, Oberursel; Hans Bohnen, Niedernhausen, all of (DE)

(73) Assignee: Targor GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/867,214

(22) Filed: Jun. 2, 1997

(30) Foreign Application Priority Data

Jun. 3, 1996 (DE) .............................................. 196 22 207

(51) Int. Cl.$^7$ ................................. C07F 5/02; C07F 5/06

(52) U.S. Cl. ................................. 568/3; 568/6; 556/170

(58) Field of Search .................................. 568/2, 3, 6, 8, 568/16, 17; 556/172, 170, 174, 178, 400, 402, 403–404

(56) References Cited

U.S. PATENT DOCUMENTS

| | | | |
|---|---|---|---|
| 5,347,024 | 9/1994 | Nickias et al. | 556/11 |
| 5,447,895 | 9/1995 | Marks et al. | 502/117 |
| 5,496,960 | 3/1996 | Piers et al. | 556/8 |
| 5,519,100 | 5/1996 | Ewen et al. | 526/134 |

FOREIGN PATENT DOCUMENTS

| | | |
|---|---|---|
| 2212668 | 2/1998 | (CA) . |
| 710 663 | 10/1995 | (EP) . |
| 0824113 | 2/1998 | (EP) . |
| 93/11172 | 6/1993 | (WO) . |
| 93/19103 | 9/1993 | (WO) . |
| 95/24268 | 9/1995 | (WO) . |
| 95/24269 | 9/1995 | (WO) . |
| 96/04319 | 2/1996 | (WO) . |
| 96/23005 | 8/1996 | (WO) . |
| 96/28480 | 9/1996 | (WO) . |
| 96/41808 | 12/1996 | (WO) . |
| 97/15581 | 5/1997 | (WO) . |
| 97/19959 | 6/1997 | (WO) . |

OTHER PUBLICATIONS

CA:81:37598 by Dungoes et al, "Silylation of gem–polychloro derivatives", J Organometal Chem 71 (3), pp. 377–392, 1974.*

CA:75:20465 by Krohmer et al "Reactions of methylenedilithium with boron conpounds", Chem Ber 104 (5), pp. 1347–1361, 1971.*

CA:123:112112 by Parks et al "Bis (pentafluorophenyl)borane: synthesis, properties, and hydroboration chemistry of a highly electrophilic borane reagent", Angew. Chem., Int Ed Engl 34 (7), pp. 809–811, 1995.*

CA:117:212550 by Kombarova et al "Kinetics of phenylpolymagnesium halide reaction with allyl bromides", Vestn. mosl univ Ser 2: Khim 33 (2) pp. 151–154, 1992.*

CA:121:147733 by Tattershall et al, "NMR evidence form new phsophorus halides", Polyhedron, 13(10), pp. 1517–1521, 1994.*

CA:115:256307 by Mochida et al, "Photochemical reactions of vinyl–, styryl– and benzyl–substituted digermanes", Bull. Chem Soc Jpn. 64(9) pp. 2772–2777, 1991.*

CA:118:124599 abs of Chem Ber by Koester 126(2) pp. 305–317, 1993.*

CA:84:58498 abs of Synthesis by Miyaura (10) pp. 669–670, 1975.*

CA;79:78871 abs of Justus Liebigs Ann Chem by Lehmkuhl (4) pp. 669–691, 1973.*

CA:70:37868 abs of Justus Liebigs Ann Chem by Koester 717 pp. 21–40, 1968.*

CA:119:250000 abs of Angew Chem by He 105(5) pp. 761–762, 1993.*

CA:119:117318 abs of Inorg chem by Wehmschulte 32 (14) pp. 2983–2984, 1993.*

(List continued on next page.)

*Primary Examiner*—Jean F Vollano
(74) *Attorney, Agent, or Firm*—Connolly Bove Lodge & Hutz LLP

(57) ABSTRACT

The present invention relates to a chemical compound of the formula I $$[R_jM-X_d-(-MR_{j-1}-\overset{\overset{\displaystyle(MR_j)_k}{|}}{\underset{\underset{\displaystyle(MR_j)_h}{|}}{X_f}}-X_e-)_i-MR_j]^{a-} \quad bA^{c+} \quad \text{(I)}$$

$$\underset{(MR_j)_g}{|}$$

where

R are, independently of one another, identical or different and are each a halogen atom or a $C_1$–$C_{40}$-group, X are, independently of one another, identical or different and are each a $C_1$–$C_{40}$-group, M are, independently of one another, identical or different and are each an element of group IIIa, of the Periodic Table of the Elements, a is an integer from 0 to 10, b is an integer from 0 to 10, c is an integer from 0 to 10 and a=b•c, d is 0 or 1, e is 0 or 1, f is 0 or 1, g is an integer from 0 to 10, h is an integer from 0 to 10, k is an integer from 0 to 10, i is an integer from 0 to 1000, j is an integer from 1 to 6 and is a cation of group Ia, IIa, IIIa or the Periodic Table of the Elements, a carbenium, oxonium or sulfonium cation or a quaternary ammonium compound.

10 Claims, No Drawings

OTHER PUBLICATIONS

CA:90:65880 abs of Angew Chem by Hoberg 90(12) pp. 1013, 1978.*

Beilstein 4051285 abs of Justus Liebigs Ann Chem by Binger 717 pp. 21–40, 1968.*

Beilstein 4054875 abs of Justus Liebigs Ann Chem by Binger 717 pp. 21–40, 1968.*

Beilstein 3881880 abs of Justus Liebigs Ann Chem by Wittig 606 pp. 1, 23, 1957.*

CA:69:43957 abs of Bull Soc Chim Fr (1) pp. 216–220 by Demarne, 1968.*

CA: 78:111501 abs of DE226193, Feb. 1973.*

CA:116:6606 abs of Metalloorg Khim by Gorobets et al 4(5) pp. 1196–1197, 1991.*

CA:112:223666 ab of J Mol Struct by Stoelevik et al 216, 105–11, 1990.*

CA:113:212052 abs of Z Naturforsch B Chem Sci by Knoerzer et al 45(7) pp. 985–989, 1990.*

CA:66:101241 abs of J Am Chem Soc 89(7) pp. 1629–1632 by Timms, 1967.*

CA:6977299 ab of J Am Chem Soc by Timms 90(17) pp. 4585–4589, 1968.*

CA:130:182889 abs of WO9906413, Feb. 1999.*

CA:71:70676 abs of J Chem Soc by Dobson et al 12 pp. 1882–1888, 1969.*

Paetzold, Peter et al: "Boron imides in the thermal decomposition of diarylazidoboranes" Chem. Ber. (1993), 116(4), pps. 1531–9, XP002119538.

Jia et al., "Protected (Fluoroary)borates as Effective Counteranions for Cationic Metallocene Polymerization Catalysts," Organometallics, 14:3135–3137 (1995).

Reetz et al., "Preparation and Catalytic Activity of Boron–Substituted Zirconocenes," Chimia, 49:501–503 (1995).

* cited by examiner

BORON COMPOUNDS AND OTHER COMPOUNDS OF GROUP IIIA

DESCRIPTION

The present invention relates to a chemical compound which can have an uncharged or ionic structure. In combination with a metallocene, this can form a novel catalyst system which is advantageously used for the polymerization of olefins. Here, the use of aluminoxanes such as methylaluminoxane (MAO) as cocatalyst can be omitted and high catalyst activities can nevertheless be achieved.

The role of cationic complexes in Ziegler-Natta polymerization using metallocenes is generally recognized (M. Bochmann, Nachr. Chem. Lab. Techn. 1993, 41, 1220). MAO as hitherto most effective cocatalyst has the disadvantage of being used in a high excess. The preparation of cationic alkyl complexes opens up the route to MAO-free catalysts having comparable activity.

The synthesis of cationic alkyl complexes is achieved by
- a) protolysis of metallocene compounds using, for example, weakly acid ammonium salts of the very stable, nonbasic tetra(pentafluorophenyl)borate anion (e.g. $[PhMe_2NH]^+[B(C_6F_5)_4]^-$),
- b) abstraction of an alkyl group from metallocene compounds with the aid of strong Lewis acids, where the Lewis acids employed can be either salts of the formula $(Ph_3C^+BR_4^-)$ or strong, uncharged Lewis acids such as $B(C_6F_5)_3$ or by
- c) oxidation of dialkylmetallocene complexes using, for example, $AgBPh_4$ or $[Cp_2Fe][BPh_4]$.

The synthesis of "cation-like" metallocene polymerization catalysts is described in J. Am. Chem. Soc. 1991, 113, 3623. In this reference, the alkyl abstraction from an alkyl metallocene compound is carried out by means of tris(pentafluorophenyl)borane. EP 427 697 claims this synthetic principle and a corresponding catalyst system comprising a neutral metallocene species (e.g. $Cp_2ZrMe_2$), a Lewis acid (e.g. $B(C_6F_5)_3$) and aluminum alkyls. A process for preparing salts of the formula $LMX^+\ XA^-$ according to the above-described principle is claimed in EP 520 732.

EP 558 158 describes zwitterionic catalyst systems which are prepared from metallocene dialkyl compounds and salts of the formula $[R_3NH]^+[BPh_4]^-$. The reaction of such a salt with, for example, $Cp_2^*ZrMe_2$ leads to the intermediate formation of a methylzirconocene cation by protolysis with elimination of methane. This reacts via C—H-activation to form the zwitterion $Cp_2^*Zr^+\text{-}(m\text{-}C_6H_4)\text{-}BPh_3^-$. In this, the Zr atom is covalently bonded to a carbon atom of the phenyl ring and is stabilized via an agostic hydrogen bond.

According to this reaction principle, the protolysis of a dialkylmetallocene species using a perfluorinated $[R_3NH]^+[B(C_6F_5)_4]^-$ salt in the first step likewise gives a cationic species, but the subsequent reaction (C—H-activation) to give zwitterionic complexes is not possible. Salts of the formula $[Cp_2Zr\text{-}R\text{-}RH]^+[B(C_6F_5)_4]^-$ are thus formed. U.S. Pat. No. 5,348,299 claims corresponding systems in which dimethylanilinium salts having perfluorinated tetraphenylborate anions are used.

A disadvantage of the systems described is that the protolysis results in formation of an amine from the ammonium salts and this coordinates to the strongly Lewis-acid cation and is thus not polymerization-active.

EP 426 637 describes a process in which the Lewis-acid $CPh_3^+$ cation is used. $B(C_6F_5)_4^-$ functions as weakly coordinating anion. This offers the advantage that after abstraction of a $CH_3$ group the resulting $CH_3CPh_3$ no longer has coordinated properties. In this way, cationic complexes of sterically unhindered metal centers can also be prepared.

WO 95/14044 describes carboboranes as constituents of catalyst systems.

Diboranes which are bridged by a hydrogen atom and an alkyl group are described in WO 95/24269. These systems have the disadvantage that the H-acid functions present therein do not rule out an interaction with the cationic system.

It is an object of the invention to find a chemical compound which has a low tendency to coordinate and which avoids the disadvantages of the prior art.

The present invention accordingly provides a chemical compound and a process for preparing this chemical compound. It further provides a catalyst system comprising at least one metallocene and at least one chemical compound of the invention as cocatalyst. In addition, a process for preparing polyolefins is described.

The chemical compound of the invention corresponds to the formula:

$$[R_jM\text{---}X_d\text{---}(MR_{j\text{-}1}\overset{(MR_j)_k}{\overset{|}{\underset{|}{\text{---}X_f\text{---}}}}X_e)_i\text{---}MR_j]^{a\text{-}}\ bA^{c+}\quad(I)$$

$$\underset{(MR_j)_g\qquad (MR_j)_h}{}$$

where

R are, independently of one another, identical or different and are each a halogen atom or a $C_1$–$C_{40}$-group such as a $C_1$–$C_{40}$-alkyl, $C_1$–$C_{40}$-haloalkyl, $C_6$–$C_{40}$-aryl, $C_6$–$C_{40}$-haloaryl, $C_7$–$C_{40}$-aralkyl or $C_7$–$C_{40}$-haloaralkyl group, X are, independently of one another, identical or different and are each a $C_1$–$C_{40}$-group such as a $C_1$–$C_{40}$-alkylene, $C_1$–$C_{40}$-haloalkylene, $C_6$–$C_{40}$-arylene, $C_6$–$C_{40}$-haloarylene, $C_7$–$C_{40}$-arylalkylene or $C_7$–$C_{40}$-haloarylalkylene, $C_2$–$C_{40}$-alkynylene, $C_2$–$C_{40}$-haloalkynylene, $C_2$–$C_{40}$-alkenylene or $C_2$–$C_{40}$-haloalkenylene group, M are, independently of one another, identical or different and are each an element of group IIa, IIIa, IVa or Va of the Periodic Table of the Elements, a is an integer from 0 to 10, b is an integer from 0 to 10, c is an integer from 0 to 10 and a=b•c, d is 0 or 1, e is 0 or 1, f is 0 or 1, g is an integer from 0 to 10, h is an integer from 0 to 10, k is an integer from 0 to 10, i is an integer from 0 to 1000, j is an integer from 1 to 6 and A is a cation of group Ia, IIa, IIIa of the Periodic Table of the Elements, a carbenium, oxonium or sulfonium cation or a quaternary ammonium compound.

When a=0, the formula represents an uncharged chemical compound; when a≧1, the formula represents a negatively charged compound having b cations $A^{c+}$ as counterions.

If the chemical compound of the formula I has a plurality of groups $MR_j$, these can be identical or different from one another.

The structural unit X connects the elements M to one another by means of covalent bonds. X can have a linear, cyclic or branched carbon skeleton.

R is preferably a $C_1$–$C_{40}$-hydrocarbon radical which can be halogenated, preferably perhalogenated, by halogens such as fluorine, chlorine, bromine or iodine, in particular a halogenated, in particular perhalogenated, $C_1$–$C_{30}$-alkyl group such as trifluoromethyl, pentachloroethyl, heptafluoroisopropyl or monofluoroisobutyl or a halogenated, in particular perhalogenated, $C_6$–$C_{30}$-aryl group such as pentafluorophenyl, heptachloronaphthyl, heptafluoronaphthyl, 1,2,3-trifluorophenyl, 1,3,5-trifluorophenyl, heptafluorotolyl, 3,5-bis(trifluoromethyl)phenyl, 2,4,6-tris(trifluoromethyl)phenyl or 2,2'(octafluoro)biphenyl.

X is preferably a $C_6$–$C_{30}$-arylene group, a $C_2$–$C_{30}$-alkenylene group or a $C_2$–$C_{30}$-alkynylene group, each of which can be halogenated, in particular perhalogenated.

Preferably j=1 or 2 when M is an element of group IIa, j=2 or 3 when M is an element of group IIIa, j=3 or 4 when M is an element of group IVa and j=4 or 5 when M is an element of the group Va. M is particularly preferably boron as an element of group IIIa.

i is preferably an integer from 0 to 6, particularly preferably 0 or 1.

a, b and c are preferably 0, 1 or 2.

g, h and k are preferably 0 or 1.

i, g, h and k are very particularly preferably 0.

As A, preference is given to carbenium ions ($R_3C^+$) or quaternary ammonium ions having an acid H function ($R_3NH^+$). Particular preference is given to quaternary ammonium salts having acid H functions.

If a≧1 and all M are boron, it is preferred that the number of boron atoms is ≦4, particularly preferably 2.

Examples of the chemical compound of the invention are:

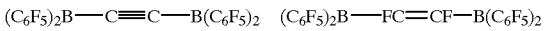
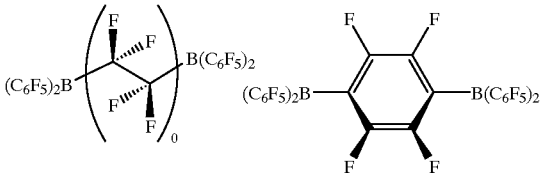
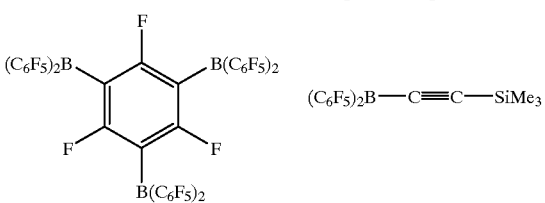
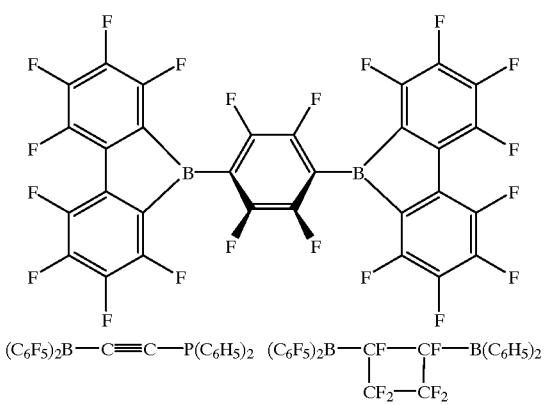

-continued

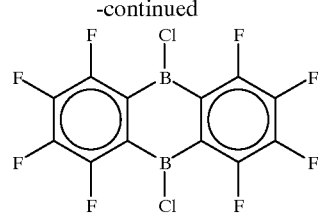
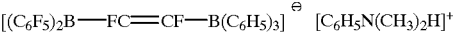
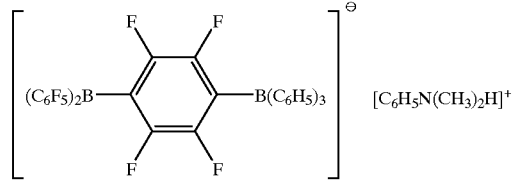
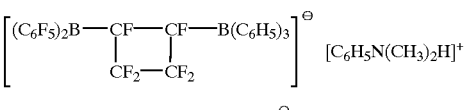
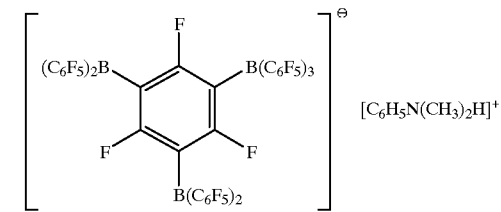
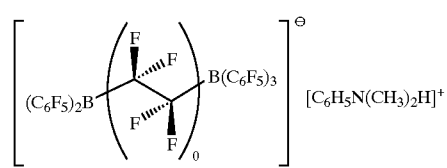

In place of the N,N-dimethylanilinium cation [$C_6H_5N(CH_3)_2H$]$^+$, the cation used can alternatively be $CPh_3^+$ o is 0 to 20.

The preparation of a chemical compound according to the invention can proceed, for example, according to the following reaction scheme:

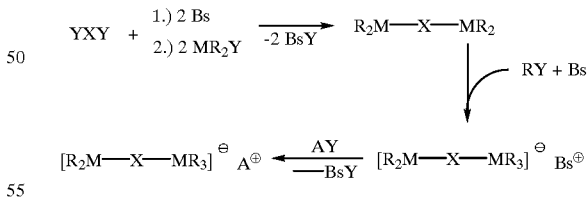

In this scheme
- X is a $C_1$–$C_{40}$-group such as a $C_1$–$C_{40}$-alkylene, $C_1$–$C_{40}$-haloalkylene, $C_6$–$C_{40}$-arylene, $C_6$–$C_{40}$-haloarylene, $C_7$–$C_{40}$-arylalkylene or $C_7$–$C_{40}$-haloarylalkylene, $C_2$–$C_{40}$-alkynylene, $C_2$–$C_{40}$-haloalkynylene, $C_2$–$C_{40}$-alkenylene or $C_2$–$C_{40}$-haloalkenylene group,
- Y are, independently of one another, identical or different and are each a leaving group, preferably a hydrogen or halogen atom,
- R are, independently of one another, identical or different and are each a halogen atom or a $C_1$–$C_{40}$-group such as a $C_1$–$C_{40}$-alkyl, $C_1$–$C_{40}$-haloalkyl, $C_6$–$C_{40}$-aryl, $C_6$–$C_{40}$-haloaryl, $C_7$–$C_{40}$-arylalkyl or $C_7$–$C_{40}$-haloarylalkyl group, Bs is a base, preferably an organolithium compound or a Grignard compound, M are identical or different and are each an element of group IIa, IIIa, IVa or Va of the Periodic Table of the Elements and A is a cation of group Ia, IIa or IIIa of the Periodic Table of the Elements, a carbenium, oxonium or sulfonium cation or a quaternary ammonium compound.

The chemical compound of the invention can be used together with metallocenes as a catalyst system. Metallocenes comprise at least one central metal atom to which at least one π-ligand, e.g. cyclopentadienyl ligand, is bonded. Preference is given to chiral metallocenes. In addition, further substituents such as halogen, alkyl, alkoxy or aryl groups can be bonded to the central metal atom. The central metal atom is preferably an element of transition group II, IV, V or VI of the Periodic Table of the Elements, in particular from transition group IV of the Periodic Table of the Elements, for example Ti, Zr or Hf. For the purposes of the present invention, cyclopentadienyl ligands are unsubstituted cyclopentadienyl radicals and substituted cyclopentadienyl radicals such as methylcyclopentadienyl, indenyl, 2-methylindenyl, 2-methyl-4-phenylindenyl, tetrahydroindenyl, benzoindenyl, fluorenyl, benzofluorenyl, tetrahydrofluorenyl and octahydrofluorenyl radicals. The π ligands, e.g. cyclopentadienyl ligands, can be bridged or unbridged, with single and multiple bridges, even via ring systems, being possible. The term metallocene also includes compounds having more than one metallocene fragment, known as multinuclear metallocenes. These can have any substitution pattern and bridging variants. The individual metallocene fragments of such multinuclear metallocenes can be either of the same type or different from one another. Examples of such multinuclear metallocenes are described, for example, in EP-A-632063, JP-A-04/80214, JP-A-04/85310, EP-A-654476.

Particular preference is given to unbridged or bridged metallocenes of the formula II,

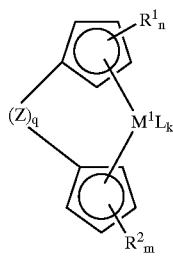

(II)

where

M1 is a metal of transition group III, IV, V or VI of the Periodic Table of the Elements, in particular Zr or Hf, $R^1$ are identical or different and are each a hydrogen atom, $SiR^3$, where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or a $C_1$–$C_{30}$-group such as $C_1$–$C_{25}$-alkyl, e.g. methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals $R^1$ can be connected to one another such that the radicals $R^1$ and the atoms of the cyclopentadienyl ring which connect them form a $C_4$–$C_{24}$-ring system, which may in turn be substituted, $R^2$ are identical or different and are each a hydrogen atom, $SiR^3$, where $R^3$ are identical or different and are each a hydrogen atom or a $C_1$–$C_{40}$-group such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or a $C_1$–$C_{30}$-group such as $C_1$–$C_{25}$-alkyl, e.g. methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, e.g. pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals $R^2$ can also be connected to one another such that the radicals $R^2$ and the atoms of the cyclopentadienyl ring which connect them form a $C_4$–$C_{24}$-ring system, which may in turn be substituted, n is 5 when q=0, and n is 4 when q=1, m is 5 when q=0, and m is 4 when q=1, L are identical or different and are each a halogen atom or a hydrocarbon radical having 1–20 carbon atoms, e.g. $C_1$–$C_{20}$-alkyl, $C_2$–$C_{20}$-alkenyl, $C_1$–$C_{20}$-alkoxy, $C_6$–$C_{14}$-aryloxy or $C_6$–$C_{40}$-aryl, k is an integer from 1 to 4, where if $M^1$=Ti, Zr or Hf, k is preferably 2, Z is a bridge structural element between the two cyclopentadienyl rings, and q is 0 or 1.

Examples of Z are groups $M^2R^4R^5$, where $M^2$ is carbon, silicon, germanium or tin and $R^4$ and $R^5$ are identical or different and are each a $C_1$–$C_{20}$-group such as $C_1$–$C_{10}$-alkyl or $C_6$–$C_{14}$-aryl. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, $o$-$C_6H_4$ or $2,2'$-$(C_6H_4)_2$. Z together with one or more radicals $R^1$ and/or $R^2$ can also form a monocyclic or polycyclic ring system.

Preference is given to chiral bridged metallocenes of the formula II, in particular those in which q is 1 and one or both cyclopentadienyl rings are substituted in such a way that they form an indenyl ring. The indenyl ring is preferably substituted, in particular in the 2; 4; 2,4,5; 2,4,6; 2,4,7 or 2,4,5,6 positions, by $C_1$–$C_{20}$-groups such as $C_1$–$C_{10}$-alkyl or $C_6$–$C_{20}$-aryl, where two or more substituents of the indenyl ring can together also form a ring system.

The following examples of metallocene serve to illustrate the present invention but do not restrict it in any way: bis(cyclopentadienyl)dimethylzirconium bis(indenyl) dimethylzirconium bis(fluorenyl)dimethylzirconium (indenyl)(fluorenyl)dimethylzirconium (3-methyl-5-naphthylindenyl)(2,7-di-tert-butylfluorenyl) dimethylzirconium (3-methyl-5-naphthylindenyl)(3,4,7-trimethoxyfluorenyl)dimethylzirconium (pentamethylcyclopentadienyl)(tetrahydroindenyl) dimethylzirconium (cyclopentadienyl)(1-octen-8-ylcyclopentadienyl)dimethylzirconium (indenyl)(1-buten-4-ylcyclopentadienyl)dimethylzirconium [1,3-bis (trimethylsilyl)cyclopentadienyl](3,4-benzofluorenyl)dimethylzirconium bis(cyclopentadienyl)dimethyltitanium dimethylsilanediylbis(indenyl)dimethylzirconium dimethylsilanediylbis(tetrahydroindenyl)dimethylzirconium dimethylsilanediyl(cyclopentadienyl)(indenyl)dimethylzirconium dimethylsilanediylbis(2-methylindenyl)dimethylzirconium dimethylsilanediylbis(2-ethylindenyl)dimethylzirconium dimethylsilanediylbis(2-methyl-4,5-benzoindenyl)dimethylzirconium dimethylsilanediylbis(2-ethyl-4,5-benzoindenyl)dimethylzirconium dimethylsilanediylbis(4,5-dihydro-8-methyl-7H-cyclopent[e]acenaphthylen-7-ylidene)dimethylzirconium dimethylsilanediyl(2-methyl-4,5-benzoindenyl)(2-methyl-4-phenylindenyl)dimethylzirconium dimethylsilanediyl(2-ethyl-4,5-benzoindenyl)(2-methyl-4-phenylindenyl)dimethylzirconium dimethylsilanediyl(2-methyl-4,5-benzoindenyl)(2-ethyl-4-phenylindenyl)dimethylzirconium dimethylsilanediyl(2-ethyl-4,5-benzoindenyl)(2-ethyl-4-naphthylindenyl)dimethylzirconium dimethylsilanediyl(2-methylindenyl)(4-phenylindenyl)dimethylzirconium dimethylsilanediylbis(2-methyl-4-phenylindenyl)dimethylzirconium dimethylsilanediylbis(2-ethyl-4-phenylindenyl)dimethylzirconium dimethylsilanediylbis(2-methyl-4,6-diisopropylindenyl)dimethylzirconium dimethylsilanediylbis(2-ethyl-4,6-diisopropylindenyl)dimethylzirconium dimethylsilanediylbis(2-methyl-4-naphthylindenyl)dimethylzirconium dimethylsilanediylbis(2-ethyl-4-naphthylindenyl)dimethylzirconium methylphenylsilanediylbis(indenyl)dimethylzirconium methylphenylsilanediyl(cyclopentadienyl)(indenyl)dimethylzirconium methylphenylsilanediylbis(tetrahydroindenyl)dimethylzirconium methylphenylsilanediylbis(2-methylindenyl)dimethylzirconium methylphenylsilanediylbis(2-ethylindenyl)dimethylzirconium methylphenylsilanediylbis(2-methyl-4,5-benzoindenyl)dimethylzirconium methylphenylsilanediylbis(2-ethyl-4,5-benzoindenyl)dimethylzirconium methylphenylsilanediylbis(4,5-dihydro-8-methyl-7H-cyclopent[e]acenaphthylen-7-ylidene)dimethylzirconium methylphenylsilanediyl(2-methyl-4,5-benzoindenyl)(2-methyl-4-phenylindenyl)dimethylzirconium methylphenylsilanediyl(2-ethyl-4,5-benzoindenyl)(2-methyl-4-phenylindenyl)dimethylzirconium methylphenylsilanediyl(2-methyl-4,5-benzoindenyl)(2-ethyl-4-phenylindenyl)dimethylzirconium methylphenylsilanediyl(2-ethyl-4,5-benzoindenyl)(2-ethyl-4-naphthylindenyl)dimethylzirconium methylphenylsilanediyl(2-methylindenyl)(4-phenylindenyl)dimethylzirconium methylphenylsilanediylbis(2-methyl-4-phenylindenyl)dimethylzirconium methylphenylsilanediylbis(2-ethyl-4-phenylindenyl)dimethylzirconium methylphenylsilanediylbis(2-methyl-4,6-diisopropylindenyl)dimethylzirconium methylphenylsilanediylbis(2-ethyl-4,6-diisopropylindenyl)dimethylzirconium methylphenylsilanediylbis(2-methyl-4-naphthylindenyl)dimethylzirconium methylphenylsilanediylbis(2-ethyl-4-naphthylindenyl)dimethylzirconium diphenylsilanediylbis(indenyl)dimethylzirconium diphenylsilanediylbis(2-methylindenyl)dimethylzirconium diphenylsilanediylbis(2-ethylindenyl)dimethylzirconium diphenylsilanediyl(cyclopentadienyl)(indenyl)dimethylzirconium diphenylsilanediylbis(2-ethyl-4,5-benzoindenyl)dimethylzirconium diphenylsilanediyl(2-methyl-4,5-benzoindenyl)(2-methyl-4-phenylindenyl)dimethylzirconium diphenylsilanediyl(2-ethyl-4,5-benzoindenyl)(2-methyl-4-phenylindenyl)dimethylzirconium diphenylsilanediyl(2-methyl-4,5-benzoindenyl)(2-ethyl-4-phenylindenyl)dimethylzirconium diphenylsilanediyl(2-ethyl-4,5-benzoindenyl)(2-ethyl-4-naphthylindenyl)dimethylzirconium diphenyisilanediyl(2-methyl-4,5-ezindenyl)(2ethyl-4-naphenylindenyl)dimethlzirconium diphenylsilanediylbis(2-methyl-4-phenylindenyl)dimethylzirconium diphenylsilanediylbis(2-ethyl-4-phenylindenyl)dimethylzirconium diphenylsilanediylbis(2-methyl-4,6-diisopropylindenyl)dimethylzirconium diphenyisilanediylbis(2-ethyl-4,6-diisopropylindenyl)dimethylzirconium diphenylsilanediylbis(2-methyl-4-naphthylindenyl)dimethylzirconium diphenylsilanediylbis(2-ethyl-4-naphthylindenyl)dimethylzirconium 1-silacyclopentane-1,1-bis(indenyl)dimethylzirconium 1-silacyclopentane-1,1-bis(2-methylindenyl)dimethylzirconium 1-silacyclopentane-1,1-bis(2-ethylindenyl)dimethylzirconium 1-silacyclopentane-1,1-bis(2-methyl-4,5-benzoindenyl)dimethylzirconium 1-silacyclopentane-1,1-bis(2-ethyl-4,5-benzoindenyl)dimethylzirconium 1-silacyclopentane-1-(2-methyl-4,5-benzoindenyl)-1-(2-methyl-4-phenylindenyl)dimethylzirconium 1-silacyclopentane-1-(2-ethyl-4,5-benzoindenyl)-1-(2-methyl-4-phenylindenyl)dimethylzirconium 1-silacyclopentane-1-(2-methyl-4,5-benzoindenyl)-1-(2-ethyl-4-phenylindenyl)dimethylzirconium 1-silacyclopentane-1-(2-ethyl-4,5-benzoindenyl)-1-(2-ethyl-4-naphthylindenyl)dimethylzirconium 1-silacyclopentane-1-(2-methylindenyl)-1-(4-phenylindenyl)dimethylzirconium 1-silacyclopentane-1,1-bis(2-methyl-4-phenylindenyl)dimethylzirconium 1-silacyclopentane-1,1-bis(2-ethyl-4-phenylindenyl)dimethylzirconium 1-silacyclopentane-1,1-bis(2-methyl-4,6-diisopropylindenyl)dimethyzirconium 1-silacyclopentane-1,1-bis(2-ethyl-4,6-diisopropylindenyl)dimethylzirconium 1-silacyclopentane-1,1-bis(2-methyl-4-naphthylindenyl)dimethylzirconium 1-silacyclopentane-1,1-bis(2-ethyl-4-naphthylindenyl)dimethylzirconium bis(cyclopentadienyl)dimethyltitanium ethylene-1,2-bis(indenyl)dimethylzirconium ethylene-1,2-bis(tetrahydroindenyl)dimethyizirconium ethylene-1-cyclopentadienyl-2-(l1-indenyl)dimethylzirconium ethylene-1-cyclopentadienyl-2-(2-indenyl)dimethylzirconium ethylene-1-cyclopentadienyl-2-(2-methyl-1-indenyl)dimethylzirconium ethylene-1,2-bis(2-methylindenyl)dimethylzirconium ethylene-1,2-bis(2-methylindenyl)dimethylzirconium ethylene-1,2-bis(2-methyl-4,5-benzoindenyl)dimethylzirconium ethylene-1,2-bis(2-ethyl-4,5-benzoindenyl)dimethylzirconium ethylene-1,2-bis(4,5-dihydro-8-methyl-7H-cyclopent[e]acenaphthylen-7-ylidene)dimethylzirconium ethylene-1-(2-methyl-4,5-benzoindenyl)-2-(2-methyl-4-phenylindenyl)dimethylzirconium ethylene-1-(2-ethyl-4,5-benzoindenyl)-2-(2-methyl-4-phenylindenyl)dimethylzirconium ethylene-1-(2-methyl-4,5-benzoindenyl)-2-(2-ethyl-4-phenylindenyl)dimethylzirconium ethylene-1-(2-ethyl-4,5-benzoindenyl)-2-(2-ethyl-4-naphthylindenyl)dimethylzirconium ethylene-1-(2-methylindenyl)-2-(4-phenylindenyl)dimethylzirconium ethylene-1,2-bis(2-methyl-4-phenylindenyl)dimethylzirconium ethylene-1,2-bis(2-ethyl-4-phenylindenyl)dimethylzirconium ethylene-1,2-bis(2-methyl-4,6-diisopropylindenyl)dimethylzirconium ethylene-1,2-bis(2-ethyl-4,6-diisopropylindenyl)dimethylzirconium ethylene-1,2-bis(2-methyl-4-naphthylindenyl)dimethylzirconium ethylene-1,2-bis(2-ethyl-4-naphthylindenyl)dimethylzirconium propylene-2,2-bis(indenyl)dimethylzirconium propylene-2-cyclopentadienyl-2-(1-indenyl)dimethylzirconium propylene-2-cyclopentadienyl-2-(4-phenyl-1-indenyl)dimethylzirconium propylene-2-cyclopentadienyl-2-(9-fluorenyl)dimethylzirconium propylene-2-cyclopentadienyl-2-(2,7-dimethoxy-9-fluorenyl)dimethylzirconium propylene-2-cyclopentadienyl-2-(2,7-di-tert-butyl-9-fluorenyl)dimethylzirconium propylene-2-cyclopentadienyl-2-(2,7-diphenyl-9-fluorenyl)dimethylzirconium propylene-2-cyclopentadienyl-2-(2,7-dimethyl-9-fluorenyl)dimethylzirconium propylene-2-(3-methylcyclopentadienyl)-2-(2,7-dibutyl-9-fluorenyl)dimethylzirconium propylene-2-(3-tert-butylcyclopentadienyl)-2-(2,7-dibutyl-9-fluorenyl)dimethylzirconium propylene-2-(3-trimethylsilylcyclopentadienyl)-2-(3,6-di-tert-butyl-9-fluorenyl)dimethylzirconium propylene-2-cyclopentadienyl-2-[2,7-bis(3-buten-1-yl)-9-fluorenyl]dimethylzirconium propylene-2-cyclopentadienyl-2-(3-tert-butyl-9-fluorenyl)dimethylzirconium propylene-2,2-bis(tetrahydroindenyl)dimethylzirconium propylene-2,2-bis(2-methylindenyl)dimethylzirconium propylene-2,2-bis(2-ethylindenyl)dimethylzirconium propylene-2,2-bis(2-methyl-4,5-benzoindenyl)dimethylzirconium propylene-2,2-bis(2-ethyl-4,5-benzoindenyl)dimethylzirconium propylene-2,2-bis(4,5-dihydro-8-methyl-7H-cyclopent[e]acenaphthylen-7-ylidene)dimethylzirconium propylene-2-(2-methyl-4,5-benzoindenyl)-2-(2-methyl-4-phenylindenyl)dimethylzirconium propylene-2-(2-ethyl-4,5-benzoindenyl)-2-(2-methyl-4-phenylindenyl)dimethylzirconium propylene-2-(2-methyl-4,5-benzoindenyl)-2-(2-ethyl-4-phenylindenyl)dimethylzirconium propylene-2-(2-ethyl-4,5-benzoindenyl)-2-(2-ethyl-4-naphthylindenyl)dimethylzirconium propylene-2-(2-methylindenyl)-2-(4-phenylindenyl)dimethylzirconium propylene-2,2-bis(2-methyl-4-phenylindenyl)dimethylzirconium propylene-2,2-bis(2-ethyl-4-phenylindenyl)dimethylzirconium propylene-2,2-bis(2-methyl-4,6-diisopropylindenyl)dimethylzirconium propylene-2,2-bis(2-ethyl-4,6-diisopropylindenyl)dimethylzirconium propylene-2,2-bis(2-methyl-4-naphthylindenyl)dimethylzirconium propylene-2,2-bis(2-ethyl-4-naphthylindenyl)dimethylzirconium 1,6-bis[methylsilylbis(2-methyl-4-phenylindenyl)dimethylzirconium]hexane 1,6-bis[methylsilylbis(2-methyl-4,5-benzoindenyl)dimethylzirconium]hexane 1,6-bis[methylsilylbis(2-ethyl-4-phenylindenyl)dimethylzirconium]hexane 1,6-bis[methylsilylbis(2-methyl-4-naphthylindenyl)dimethylzirconium]hexane 1,6-bis[methylsilylbis(2-methyl-4,6-diisopropylindenyl)dimethylzirconium]hexane 1,6-bis[methylsilyl(2-methyl-4-phenylindenyl)(4,5-benzoindenyl)dimethylzirconium]hexane 1-[methylsilylbis(tetrahydroindenyl)dimethylzirconium]-6-[ethylstannyl(cyclopentadienyl)(fluorenyl)dimethylzirconium]hexane 1,6-disila-1,1,6,6-tetramethyl-1,6-bis[methylsilylbis(2-methyl-4-phenylindenyl)zirkoniumdimethyl]hexane 1,4-disila-1,4-bis[methylsilylbis(2-methyl-4-phenylindenyl)dimethylzirconium]cyclohexane [1,4-bis(1-indenyl)-1,1,4,4-tetramethyl-1,4-disilabutane]bis(pentamethylcyclopentadienyldimethylzirconium) [1,4-bis(9-fluorenyl)-1,1,4,4-tetramethyl-1,4-disilabutane]bis(cyclopentadienyldimethylzirconium) [1,4-bis(1-indenyl)-1,1,4,4-tetramethyl-1,4-disilabutane]bis(cyclopentadienyldimethylzirconium) [1-(1-indenyl)-6-(2-phenyl-1-indenyl)-1,1,6,6-tetraethyl-1,6-disila-4-oxahexane]bis(tert-butylcyclopentadienyldimethylzirconium) [1,10-bis(2,3-dimethyl-1-indenyl)-1,1,10,10-tetramethyl-1,10-digermadecane]bis(2-methyl-4-phenylindenyidimethylzirconium) (1-methyl-3-tert-butylcyclopentadienyl)(1-phenyl-4-methoxy-7-chlorofluorenyl)dimethylzirconium (4,7-dichloroindenyl)(3,6-dimesitylfluorenyl)dimethylzirconium bis(2,7-di-tert-butyl-9-cyclohexylfluorenyl)dimethylzirconium (2,7-dimesitylfluorenyl)[2,7-bis(1-naphthyl)fluorenyl]dimethylzirconium dimethylsilylbis(fluorenyl)dimethylzirconium dibutylstannylbis(2-methylfluorenyl)dimethylzirconium 1,1,2,2-tetraethyldisilanediyl(2-methylindenyl)(4-phenylfluorenyl)dimethylzirconium propylene-1-(2-indenyl)-2-(9-fluorenyl)dimethylzirconium 1,1-dimethyl-1-silaethylenebis(fluorenyl)dimethylzirconium [4-(cyclopentadienyl)-4,7,7-trimethyl(tetrahydroindenyl)]dimethylzirconium [4-(cyclopentadienyl)-4,7-dimethyl-7-phenyl(5,6-dimethyltetrahydroindenyl)]dimethylzirconium [4-(cyclopentadienyl)-4,7-dimethyl-7-(1-naphthyl)(7-phenyltetrahydroindenyl)]dimethylzirconium [4-(cyclopentadienyl)4,7-dimethyl-7-butyl(6,6-diethyltetrahydroindenyl)]dimethylzirconium [4-(3-tert-butylcyclopentadienyl)-4,7,7-trimethyl(tetrahydroindenyl)]dimethylzirconium [4-(1-indenyl)4,7,7-trimethyl(tetrahydroindenyl)]dimethylzirconium bis(cyclopentadienyl)dimethylhafnium bis(indenyl)dimethylvanadium bis(fluorenyl)dimethylscandium (indenyl)(fluorenyl)dimethylniobium (2-methyl-7-naphthylindenyl)(2,6-di-tert-butylfluorenyl)dimethyltitanium (pentamethylcyclopentadienyl)(tetrahydroindenyl)methylhafnium bromide (cyclopentadienyl)(1-octen-8-ylcyclopentadienyl)dimethylhafnium (indenyl)(2-buten-4-ylcyclopentadienyl)dimethyltitanium [1,3-bis(trimethylsilyl)cyclopentadienyl](3,4-benzofluorenyl)dimethyiniobium bis(cyclopentadienyl)dimethyltitanium dimethylsilanediylbis(indenyl)dimethyltitanium dimethylsilanediylbis(tetrahydroindenyl)dimethylhafnium dimethylsilanediyl(cyclopentadienyl)(indenyl)dimethyltitanium dimethylsilanediylbis(2-methylindenyl)dimethylhafnium dimethylsilanediylbis(2-ethylindenyl)methylscandium dimethylsilanediylbis(2-butyl-4,5-benzoindenyl)dimethylniobium dimethylsilanediylbis(2-ethyl-4,5-benzoindenyl)dimethyltitanium dimethylsilanediylbis(4,5-dihydro-8-methyl-7H-cyclopent[e]acenaphthylen-7-ylidene)dimethyltitanium dimethylsilanediyl(2-methyl-4,5-benzoindenyl)(2-methyl-4-phenylindenyl)dimethyltitanium dimethylsilanediyl(2-ethyl-4,5-benzoindenyl)(2-methyl-4-phenylindenyl)dimethylhafnium dimethylsilanediyl(2-methyl-4,5-benzoindenyl)(2-ethyl-4-phenylindenyl)methylscandium dimethylsilanediyl(2-ethyl-4,5-benzoindenyl)(2-ethyl-4-naphthylindenyl)dimethyltitanium dimethylsilanediyl(2-methylindenyl)(4-phenylindenyl)dimethylhafnium dimethylsilanediylbis(2-methyl-4-phenylindenyl)dimethylniobium dimethylsilanediylbis(2-ethyl-4-phenylindenyl)dimethylvanadium dimethylsilanediylbis(2-methyl-4,6-diisopropylindenyl)dimethylhafnium dimethylsilanediylbis(2-ethyl-4,6-diisopropylindenyl)dimethylvanadium dimethylsilanediylbis(2-methyl-4-naphthylindenyl)methylhafnium bromide dimethylsilanediylbis(2-ethyl-4-naphthylindenyl)dimethyltitanium methylphenylsilanediylbis(indenyl)dimethyltitanium methylphenylsilanediyl(cyclopentadienyl)(indenyl)dimethylhafnium methylphenylsilanediylbis(tetrahydroindenyl)dimethylhafnium methylphenylsilanediylbis(2-methylindenyl)dimethyltitanium methylphenylsilanediylbis(2- ethylindenyl)dimethylhafnium methylphenylsilanediylbis(2-methyl-4,5-benzoindenyl)dimethylhafnium methylphenylsilanediylbis(2-ethyl-4,5-benzoindenyl)dimethylvanadium methylphenylsilanediylbis(4,5-dihydro-8-methyl-7H-cyclopent[e]acenaphthylen-7-ylidene) dimethyltitanium methylphenylsilanediyl(2-methyl-4,5-benzoindenyl)(2-methyl-4-phenylindenyl)methyltitanium bromide methylphenylsilanediyl(2-ethyl-4,5-benzoindenyl)(2-methyl-4-phenylindenyl)dimethyltitanium methylphenylsilanediyl(2-methyl-4,5-benzoindenyl)(2-ethyl-4-phenylindenyl)dimethylhafnium methylphenylsilanediyl(2-ethyl-4,5-benzoindenyl)(2-ethyl-4-naphthylindenyl)dimethylhafnium methylphenylsilanediyl(2-methylindenyl)(4-phenylindenyl)dimethyltitanium methylphenylsilanediylbis(2-methyl-4-phenylindenyl)dimethylhafnium methylphenylsilanediylbis(2-ethyl-4-phenylindenyl)dimethylvanadium methylphenylsilanediylbis(2-methyl-4,6-diisopropylindenyl)dimethyltitanium methylphenyisilanediylbis(2-ethyl-4,6-diisopropylindenyl)dimethylhafnium methylphenylsilanediylbis(2-methyl-4-naphthylindenyl)dimethylhafnium methylphenylsilanediylbis(2-ethyl-4-naphthylindenyl)dimethyltitanium diphenylsilanediylbis(indenyl)dimethyltitanium diphenylsilanediylbis(2-methylindenyl)dimethylhafnium diphenylsilanediylbis(2-ethylindenyl)dimethyltitanium diphenylsilanediyl(cyclopentadienyl)(indenyl)dimethylhafnium diphenylsilanediylbis(2-methyl-4,5-benzoindenyl)dimethyltitanium diphenylsilanediylbis(2-ethyl-4,5-benzoindenyl)dimethylhafnium diphenylsilanediyl(2-methyl-4,5-benzoindenyl)(2-methyl-4-phenylindenyl)dimethylhafnium diphenyisilanediyl(2-ethyl-4,5-benzoindenyl)(2-methyl-4-phenylindenyl)dimethyltitanium diphenyisilanediyl(2-methyl-4,5-benzoindenyl)(2-ethyl-4-phenylindenyl)dimethylhafnium diphenylsilanediyl(2-ethyl-4,5-benzoindenyl)(2-ethyl-4-naphthylindenyl)dimethyltitanium diphenylsilanediyl(2-methylindenyl)(4-phenylindenyl)dimethyltitanium diphenylsilanediylbis(2-methyl-4-phenylindenyl)dimethyltitanium diphenylsilanediylbis(2-ethyl-4-phenylindenyl)dimethylihafnium diphenylsilanediylbis(2-ethyl-4,6-diisopropylindenyl)dimethylhafnium diphenylsilanediylbis(2-methyl-4-naphthylindenyl)dimethylhafnium diphenylsilanediylbis(2-ethyl-4-naphthylindenyl)dimethyltitanium 1-silacyclopentane-1,1-bis(indenyl)dimethylhafnium 1-silacyclopentane-1,1-bis(2-methylindenyl)dimethylhafnium 1-silacyclopentane-1,1-bis(2-ethylindenyl)dimethylhafnium 1-silacyclopentane-1,1-bis(2-methyl-4,5-benzoindenyl)dimethyltitanium 1-silacyclopentane-1,1-bis(2-ethyl-4,5-benzoindenyl)dimethylhafnium 1-silacyclopentane-1-(2-methyl-4,5-benzoindenyl)-1-(2-methyl-4-phenylindenyl)methylscandium 1-silacyclopentane-1-(2-ethyl-4,5-benzoindenyl)-1-(2-methyl-4-phenylindenyl)dimethylhafnium 1-silacyclopentane-1-(2-methyl-4,5-benzoindenyl)-1-(2-ethyl-4-phenylindenyl)dimethyltitanium 1-silacyclopentane-1-(2-ethyl-4,5-benzoindenyl)-1-(2-ethyl-4-naphthylindenyl)dimethylhafnium 1-silacyclopentane-1-(2-methylindenyl)-1-(4-phenylindenyl)dimethylhafnium 1-silacyclopentane-1,1-bis(2-methyl-4-phenylindenyl)dimethylhafnium 1-silacyclopentane-1,1-bis(2-ethyl-4-phenylindenyl)methyltitanium bromide 1-silacyclopentane-1,1-bis(2-methyl-4,6-diisopropylindenyl)dimethyltitanium 1-silacyclopentane-1,1-bis(2-ethyl-4,6-diisopropylindenyl)dimethyltitanium 1-silacyclopentane-1,1-bis(2-methyl-4-naphthylindenyl)methylscandium 1-silacyclopentane-1,1-bis(2-ethyl-4-naphthylindenyl)dimethyihafnium bis(cyclopentadienyl)dimethyltitanium ethylene-1,2-bis(indenyl)methylscandium ethylene-1,2-bis(tetrahydroindenyl)dimethyltitanium ethylene-1-cyclopentadienyl-2-(1-indenyl)dimethylhafnium ethylene-1-cyclopentadienyl-2-(2-indenyl)methyltitanium bromide ethylene-1-cyclopentadienyl-2-(2-methyl-1-indenyl)dimethylhafnium ethylene-1,2-bis(2-methylindenyl)dimethylhafnium ethylene-1,2-bis(2-ethylindenyl)dimethylhafnium ethylene-1,2-bis(2-methyl-4,5-benzoindenyl)dimethylhafnium ethylene-1,2-bis(2-ethyl-4,5-benzoindenyl)dimethyltitanium ethylene-1,2-bis(4,5-dihydro-8-methyl-7H-cyclopent[e]acenaphthylen-7-ylidene)dimethyltitanium ethylene-1-(2-methyl-4,5-benzoindenyl)-2-(2-methyl-4-phenylindenyl)dimethyltitanium ethylene-1-(2-ethyl-4,5-benzoindenyl)-2-(2-methyl-4-phenylindenyl)dimethyltitanium ethylene-1-(2-methyl-4,5-benzoindenyl)-2-(2-ethyl-4-phenylindenyl)methylscandium ethylene-1-(2-ethyl-4,5-benzoindenyl)-2-(2-ethyl-4-naphthylindenyl)dimethylhafnium ethylene-1-(2-methylindenyl)-2-(4-phenylindenyl)dimethyltitanium ethylene-1,2-bis(2-methyl-4-phenylindenyl)dimethylhafnium ethylene-1,2-bis(2-ethyl-4-phenylindenyl)dimethylhafnium ethylene-1,2-bis(2-methyl-4,6-diisopropylindenyl)dimethylhafnium ethylene-1,2-bis(2-ethyl-4,6-diisopropylindenyl)dimethyltitanium ethylene-1,2-bis(2-methyl-4-naphthylindenyl)dimethyltitanium ethylene-1,2-bis(2-ethyl-4-naphthylindenyl)dimethylhafnium propylene-2,2-bis(indenyl)dimethylhafnium propylene-2-cyclopentadienyl-2-(1-indenyl)dimethyltitanium propylene-2-cyclopentadienyl-2-(4-phenyl-1-indenyl)dimethyltitanium propylene-2-cyclopentadienyl-2-(9-fluorenyl)dimethylhafnium propylene-2-cyclopentadienyl-2-(2,7-dimethoxy-9-fluorenyl)dimethylhafnium propylene-2-cyclopentadienyl-2-(2,7-di-tert-butyl-9-fluorenyl)dimethylhafnium propylene-2-cyclopentadienyl-2-(2,7-dibromo-9-fluorenyl)dimethyltitanium propylene-2-cyclopentadienyl-2-(2,7-diphenyl-9-fluorenyl)dimethylhafnium propylene-2-cyclopentadienyl-2-(2,7-dimethyl-9-fluorenyl)dimethyltitanium propylene-2-(3-methylcyclopentadienyl)-2-(2,7-dibutyl-9-fluorenyl)dimethylhafnium propylene-2-(3-tert-butylcyclopentadienyl)-2-(2,7-dibutyl-9-fluorenyl)dimethyltitanium propylene-2-(3-trimethylsilylcyclopentadienyl)-2-(3,6-di-tert-butyl-9-fluorenyl)dimethyltitanium propylene-2-cyclopentadienyl-2-[2,7-bis(3-buten-1-yl)-9-fluorenyl]dimethylhafnium propylene-2-cyclopentadienyl-2-(3-tert-butyl-9-fluorenyl)dimethyltitanium propylene-2,2-bis(tetrahydroindenyl)dimethylhafnium propylene-2,2-bis(2-methylindenyl)dimethylhafnium propylene-2,2-bis(2-ethylindenyl)dimethyltitanium propylene-2,2-bis(2-methyl-4,5-benzoindenyl)dimethyltitanium propylene-2,2-bis(2-ethyl-4,5-benzoindenyl)dimethylhafnium propylene-2,2-bis(4,5-dihydro-8-methyl-7H-cyclopent[e]acenaphthylen-7-ylidene)dimethylhafnium propylene-2-(2-methyl-4,5-benzoindenyl)-2-(2-methyl-4-phenylindenyl)dimethylhafnium propylene-2-(ethyl-4,5-benzoindenyl)-2-(2-methyl-4-phenylindenyl)dimethyltitanium propylene-2-(2-methyl-4,5-benzoindenyl)-2-(2-ethyl-4-phenylindenyl)dimethylhafnium propylene-2-(2-ethyl-4,5-benzoindenyl)-2-(2-ethyl-4-naphthylindenyl)dimethyltitanium propylene-2-(2-methylindenyl)-2-(4-phenylindenyl)dimethylhafnium propylene-2,2-bis(2-methyl-4-phenylindenyl)dimethyltitanium propylene-2,2-bis(2-ethyl-4-phenylindenyl)dimethylhafnium propylene-2,2-bis(ethyl-4,6-diisopropylindenyl)dimethyltanium propylene-2,2-bis (2-ethyl-4-diphtoylindenyl)dimethyltafnium propylene-2,2-bis(2-methyl-4-napthylindenyl)dimethyltitanium propylene-2,2-bis(2-ethyl-4-napthyindenrylney) dimethyltafnium 1,6-bis[methylsilybis(2-methyl-4-phenylindenyl)dimethylhiafnium]hexane 1,6-bis[methylsilylbis(2-methyl-4,5-phenylindenyl)dimethylhafnium]hexane 1,6-bis[methylsilylbis(2-ethyl-4-phenylindenyl)dimethyltitanium]hexane 1,6-bis[methylsilylbis(2-methyl-4-napthylindenyl)dimethylhafnium]hexane 1,6-bis[methylsilylbis(2-methyl-4,6-diisopropylindenyl)dimethylhafnium]hexane 1,6-bis[methylstannyl(2-methyl-4-phenylindenyl)(4,5-benzoindenyl)dimethyl-titanium]hexane 1-[methylsilybis(tetrahydroindenyl)dimethylhafnium]-6-[ethylstannyl(cyclopentadienyl)-(fluorenyl)dimethyltitanium]hexane 1,6-disila-1,1,6,6-tetramethyl-1,6-bis[methylsilylbis(2-methyl-4-phenylindenyl)dimethylhafnium]hexane 1,4-disila-1,4-bis[methylsilylbis(2-methyl-4-phenylindenyl)dimethylhafnium]cyclohexane [1,4-bis(1-indenyl)-1,1,4,4-tetramethyl-1,4-disilabutane]bis(pentamethylcyclopentadienyldimethylhafnium) [1,4-bis(9-fluorenyl)-1,1,4,4-tetramethyl-1,4-disilabutane]bis(cyclopentadienyldimethylhafnium) [1,4-bis(1-indenyl)-1,1,4,4-tetramethyl-1,4-disilabutane]bis(cyclopentadienyldimethyltitanium) [1-(1-indenyl)-6-(2-phenyl-1-indenyl)-1,1,6,6-tetraethyl-1,6-disila-4-oxahexane]bis(tert-butylcyclopentadienyldimethyltitanium) [1,10-bis(2,3-dimethyl-1-indenyl)-1,1,10,10-tetramethyl-1,10-digermadecane]bis(2-methyl-4-phenylindenyldimethylhafnium) (1-methyl-3-tert-butylcyclopentadienyl)(1-phenyl-4-methoxy-7-chlorofluorenyl)dimethyltitanium (4,7-dichloroindenyl)(3,6-dimesitylfluorenyl)dimethyltitanium bis(2,7-di-tert-butyl-9-cyclohexylfluorenyl)dimethylhafnium (2,7-dimesitylfluorenyl)[2,7-bis(1-naphthyl)fluorenyl]dimethylhafnium dimethylsilylbis(fluorenyl)dimethyltitanium dibutylstannylbis(2-methylfluorenyl)dimethylhafnium 1,1,2,2-tetraethyldisilanediyl(2-methylindenyl)(4-phenylfluorenyl)dimethyltitanium propylene-1-(2-indenyl)-2-(9-fluorenyl)dimethylhafnium 1,1-dimethyl-1-silaethylenebis(fluorenyl)dimethyltitanium [4-(cyclopentadienyl)-4,7,7-trimethyl(tetrahydroindenyl)]dimethyltitanium [4-(cyclopentadienyl)-4,7-dimethyl-7-phenyl(5,6-dimethyltetrahydroindenyl)]dimethylhafnium [4-(cyclopentadienyl)-4,7-dimethyl-7-(1-naphthyl)(7-phenyltetrahydroindenyl)]dimethyltitanium [4-(cyclopentadienyl)-4,7-dimethyl-7-butyl(6,6-diethyltetrahydroindenyl)]dimethylhafnium [4-(3-tert-butylcyclopentadienyl)-4,7,7-trimethyl(tetrahydroindenyl)]dimethylhafnium [4-(1-indenyl)-4,7,7-trimethyl(tetrahydroindenyl)]dimethyltitanium bis(cyclopentadienyl)zirconium dichloride bis(indenyl)zirconium dichloride bis(fluorenyl)zirconium dichloride (indenyl)(fluorenyl)zirconium dichloride bis(cyclopentadienyl)titanium dichloride dimethylsilanediylbis(indenyl)zirconium dichloride dimethylsilanediylbis(tetrahydroindenyl)zirconium dichloride dimethylsilanediylbis(cyclopentadienyl)(indenyl)zirconium dichloride dimethylsilanediylbis(2-methylindenyl)zirconium dichloride dimethylsilanediylbis(2-ethylindenyl)zirconium dichloride dimethylsilanediylbis(2-methyl-4,5-benzoindenyl)zirconium dichloride dimethylsilanediylbis(2-ethyl-4,5-benzoindenyl)zirconium dichloride dimethylsilanediylbis(2-methyl-4-phenylindenyl)zirconium dichloride dimethylsilanediylbis(2-ethyl-4-phenylindenyl)zirconium dichioride dimethylsilanediylbis(2-methyl-4,6-diisopropylindenyl)zirconium dichloride ethylene-1,2-bis(indenyl)zirconium dichioride ethylene-1,2-bis(tetrahydroindenyl)zirconium dichloride ethylene-1,2-bis(2-methylindenyl)zirconium dichloride ethylene-1,2-bis(2-ethylindenyl)zirconium dichloride ethylene-1,2-bis(2-methyl-4,5-benzoindenyl)zirconium dichioride ethylene-1,2-bis(2-methyl-4-phenylindenyl)zirconium dichloride ethylene-1,2-bis(2-ethyl-4-phenylindenyl)zirconium dichloride ethylene-1,2-bis(2-methyl-4,6-diisopropylindenyl)zirconium dichloride propylene-2,2-bis(indenyl)zirconium dichloride propylene-2,2-(cyclopentadienyl)(indenyl)zirconium dichloride propylene-2,2-(cyclopentadienyl)(fluorenyl)zirconium dichloride bis(cyclopentadienyl)($\eta^4$-butadiene)zirconium bis(methylcyclopentadienyl)($\eta^4$-butadiene)zirconium bis(n-butyl-cyclopentadienyl)($\eta^4$-butadiene)zirconium bisindenyl($\eta^4$-butadiene)zirconium (tert-butylamido)dimethyl(tetramethyl-$\eta^5$-cyclopentadienyl)silane($\eta^4$-butadiene)zirconium bis(2-methylbenzoindenyl)($\eta^4$-butadiene)zirconium dimethylsilanediylbis(2-methyl-indenyl)($\eta^4$-butadiene)zirconium dimethylsilanediylbisindenyl($\eta^4$-butadiene)zirconium dimethylsilanediylbis(2-methylbenzoindenyl)($\eta^4$-butadiene)zirconium dimethylsilanediyl(2-methylbenzoindenyl)(2-methyl-indenyl)($\eta^4$-butadiene)zirconium dimethylsilanediyl(2-methylbenzoindenyl)(2-methyl-4-phenylindenyl)($\eta^4$-butadiene)zirconium dimethylsilanediyl(2-methylindenyl)(4-phenylindenyl)($\eta^4$-butadiene)zirconium dimethylsilanediylbis(2-methyl-4-phenyl-indenyl)($\eta^4$-butadiene)zirconium dimethylsilanediylbis(2-methyl-4,6-diisopropyl-indenyl)($\eta4$-butadiene)zirconium dimethylsilanediylbis(2-methyl-4-naphthyl-indenyl)($\eta^4$-butadiene)zirconium isopropylidene(cyclopentadienyl)(fluorenyl)($\eta^4$-butadiene)zirconium isopropylidene(cyclopentadienyl)(inden)($\eta^4$-butadiene)zirconium [4-$\eta$5-cyclopentadienyl)-4,7,7-trimethyl-($\eta$5-4,5,6,7-tetrahydroindenyl)($\eta^4$-butadiene)zirconium dimethylsilanediylbis(2-methyl-indenyl)($\eta^4$-butadiene)zirconium dimethylsilanediylbisindenyl($\eta^4$-butadiene)zirconium dimethylsilanediylbis(2-methylbenzoindenyl)($\eta^4$-butadiene)zirconium dimethylsilanediyl(2-methylbenzoindenyl)(2-methyl-indenyl)($\eta^4$-butadiene)zirconium dimethylsilanediyl(2-methylbenzoindenyl)(2-methyl-4-phenylindenyl)($\eta^4$-butadiene)zirconium dimethylsilanediyl(2-methylindenyl)(4-phenylindenyl)($\eta^4$-butadiene)zirconium dimethylsilanediylbis(2-methyl-4-phenylindenyl)($\eta4$-butadiene)zirconium dimethylsilanediylbis(2-methyl-4,6-diisopropylindenyl)($\eta^4$-butadiene)zirconium dimethylsilanediylbis(2-methylindenyl)($\eta^4$-butadiene)zirconium dimethylsilanediylbisindenyl($\eta^4$-butadiene)zirconium dimethylsilanediylbis(2-methylbenzoindenyl)($\eta^4$-butadiene)zirconium dimethylsilanediyl(2-methylbenzoindenyl)(2-methylindenyl)($\eta^4$-butadiene)zirconium dimethylsilanediyl(2-methylbenzoindenyl)(2-methyl-4-phenylindenyl)($\eta^4$-butadiene)zirconium dimethylsilanediyl(2-methylindenyl)(4-phenylindenyl)($\eta^4$-butadiene)zirconium dimethylsilanediylbis(2-methyl-4-phenylindenyl)($\eta4$-butadiene)zirconium dimethylsilanediylbis(2-methyl-4,6-diisopropylindenyl)($\eta^4$-butadiene)zirconium dimethylsilanediylbis(2-methyl-4-naphthylindenyl)($\eta^4$-butadiene)zirconium dimethylsilanediylbis(2-methylindenyl)($\eta^4$-butadiene)zirconium dimethylsilanediylbisindenyl($\eta^4$-butadiene)zirconium dimethylsilanediylbis(2-methylbenzoindenyl)($\eta4$-butadiene)zirconium dimethylsilanediyl(2-methylbenzoindenyl)(2-methylindeny1)($\eta^4$-butadiene)zirconium dimethylsilanediyl(2-methylbenzoindenyl)(2-methyl-4-phenylindenyl)($\eta4$-butadiene)zirconium dimethylsilanediyl(2-methylindenyl)(4-phenylindenyl)($\eta^4$-butadiene)zirconium dimethylsilanediylbis(2-methyl-4-phenylindenyl)($\eta^4$-butadiene)zirconium dimethylsilanediylbis(2-methyl-4,6-diisopropylindenyl)($\eta^4$-butadiene)zirconium dimethylsilanediylbis(2-methyl-4-naphthylindenyl)($\eta^4$-butadiene)zirconium methylphenylmethylene(fluorenyl)(cyclopentadienyl)($\eta^4$-butadiene)zirconium diphenylmethylene(fluorenyl)(cyclopentadienyl)($\eta^4$-butadiene)zirconium isopropylidene(3-methylcyclopentadienyl)(fluorenyl)($\eta^4$-butadiene)zirconium dimethylsilanediyl(3-tert-butylcyclopentadienyl)(fluorenyl)($\eta^4$-butadiene)zirconium diphenyisilanediyl(3-(trimethylsilyl)cyclopentadienyl)(fluorenyl)($\eta$4-butadiene)zirconium phenylmethylsilanediyibis(2-methylindenyl)($\eta^4$-butadiene)zirconium phenylmethylsilanediylbisindenyl($\eta^4$-butadiene)zirconium phenylmethylsilanediylbis(2-methyl-4,5-benzoindenyl)($\eta^4$-butadiene)zirconium phenylmethylsilanediyl(2-methyl-4,5-benzoindenyl)(2-methyl-indenyl)($\eta^4$-butadiene)zirconium phenylmethylsilanediyl(2-methyl-4,5-benzoindenyl)(2-methyl-4-phenylindenyl)($\eta^4$-butadiene)zirconium phenylmethylsilanediyl(2-methylindenyl)(4-phenylindenyl)($\eta^4$-butadiene)zirconium phenylmethylsilanediylbis(2-methyl-4-phenylindenyl)($\eta^4$-butadiene)zirconium phenylmethylsilanediylbis(2-ethyl-4-phenylindenyl)($\eta^4$-butadiene)zirconium phenylmethylsilanediylbis(2-methyl-4,6-diisopropylindenyl)($\eta^4$-butadiene)zirconium phenylmethylsilanediylbis(2-methyl-4-naphthylindenyl)($\eta^4$-butadiene)zirconium ethylenebis(2-methylindenyl-butadiene)zirconium ethylenebisindenyl($\eta^4$-butadiene)zirconium ethylenebis(2-methyl-4,5-benzoindenyl)($\eta^4$-butadiene)zirconium ethylene(2-methyl-4,5-benzoindenyl)(2-methylindenyl)($\eta^4$-butadiene)zirconium ethylene(2-methyl-4,5-benzoindenyl)(2-methyl-4-phenylindenyl)($\eta^4$-butadiene)zirconium ethylene(2-methylindenyl)(4-phenylindenyl)($\eta^4$-butadiene)zirconium ethylenebis(2-methyl-4,5-benzoindenyl)($\eta^4$-butadiene)zirconium ethylenebis(2-methyl-4-phenylindenyl)($\eta$4-butadiene)zirconium ethylenebis(2-methyl-4,6-diisopropylindenyl)($\eta^4$-butadiene)zirconium ethylenebis(2-methyl-4-naphthylindenyl)($\eta^4$-butadiene)zirconium ethylenebis(2-ethyl-4-phenylindenyl)($\eta^4$-butadiene)zirconium ethylenebis(2-ethyl-4,6-diisopropylindenyl)($\eta^4$-butadiene)zirconium ethylenebis(2-ethyl-4-naphthylindenyl)($\eta^4$-butadiene)zirconium dimethylsilanediylbis(2-ethyl-4-phenylindenyl)($\eta^4$-butadiene)zirconium dimethylsilanediylbis(2,3,5-trimethylcyclopentadienyl)($\eta^4$-butadiene)zirconium 1,6-{bis[methylsilylbis(2-methyl-4-phenylindenyl)($\eta^4$-butadiene)zirconium]}hexane 1,6-{bis[methylsilylbis(2-ethyl-4-phenylindenyl)($\eta^4$-butadiene)zirconium]}hexane 1,6-{bis[methylsilylbis(2-methyl-4-naphthylindenyl)($\eta^4$-butadiene)zirconium]}hexane 1,6-{bis[methylsilylbis(2-methyl-4,5-benzoindenyl)($\eta^4$-butadiene)zirconium]}hexane 1,6-{bis[methylsilyl(2-methyl-4-phenyl-indenyl)(2-methylindenyl)($\eta^4$-butadiene)zirconium]}hexane 1,2-{bis[methylsilylbis(2-methyl-4-phenylindenyl)($\eta$4-butadiene)zirconium]}ethane 1,2-{bis(methylsilylbis(2-ethyl-4-phenylindenyl)($\eta^4$-butadiene)zirconium]}ethane 1,2-{bis[methylsilylbis(2-methyl-4-naphthylindenyl)($\eta^4$-butadiene)zirconium]}ethane 1,2-{bis[methylsilylbis(2-methyl-4,5-benzoindenyl)($\eta^4$-butadiene)zirconium]}ethane 1,2-{bis[methylsilyl(2-methyl-4-phenylindenyl)(2-methylindenyl)($\eta^4$-butadiene)zirconium]}ethane.

The present invention also provides a catalyst comprising at least one transition metal compound according to the invention as cocatalyst and at least one metallocene, and also a process for preparing an olefin polymer by polymerization of at least one olefin in the presence of this catalyst according to the invention. The polymerization can be a homopolymerization or a copolymerization.

Preference is given to polymerizing olefins of the formula $R^\alpha$—CH=CH—$R^\beta$, where $R^\alpha$ and $R^\beta$ are identical or different and are each a hydrogen atom, a halogen atom, an alkoxy, hydroxy, alkylhydroxy, aldehyde, carboxylic acid or carboxylic ester group or a saturated or unsaturated hydrocarbon radical having from 1 to 20 carbon atoms, in particular from 1 to 10 carbon atoms, which may be substituted by an alkoxy, hydroxy, alkylhydroxy, aldehyde, carboxylic acid or carboxylic ester group, or $R^\alpha$ and $R^\beta$ together with the atoms connecting them form one or more rings. Examples of such olefins are 1-olefins such as ethylene, propylene, 1-butene, 1-hexene, 4-methyl-1-pentene, 1-octene, styrene, cyclic olefins such as norbornene, vinylnorbornene, tetracyclododecene, ethylidenenorbornene, dienes such as 1,3-butadiene or 1,4-hexadiene, biscyclopentadiene or methyl methacrylate.

Particular preference is given to homopolymerizing propylene or ethylene, copolymerizing ethylene with one or more $C_3$–$C_{20}$-1-olefins, in particular propylene, and/or one or more $C_4$–$C_{20}$-dienes, in particular 1,3-butadiene, or copolymerizing norbornene and ethylene.

The polymerization is preferably carried out at a temperature of from −60 to 300° C., particularly preferably from 30 to 250° C. The pressure is from 0.5 to 2500 bar, preferably from 2 to 1500 bar. The polymerization can be carried out continuously or batchwise, in one or more stages, in solution, in suspension, in the gas phase or in a supercritical medium.

The compound of the invention can be applied to supports either alone or together with a metallocene. Suitable support materials are, for example, silica gels, aluminum oxides, solid aluminoxane or other inorganic support materials such as magnesium chloride. Another suitable support material is polyolefin powder in finely divided form.

The supported system can be resuspended as powder or while still moist with solvent and be metered as suspension in an inert suspension medium into the polymerization system.

A prepolymerization can be carried out with the aid of the catalyst of the invention. For the prepolymerization, preference is given to using the (or one of the) olefin(s) used in the polymerization.

To prepare olefin polymers having a broad molecular weight distribution, preference is given to using catalyst systems comprising two or more different metallocenes.

To remove catalyst poisons present in the olefin, purification using an aluminum alkyl, for example trimethylaluminum, triethylaluminum or triisobutylaluminum is advantageous. This purification can be carried out either in the polymerization system itself or the olefin is brought into contact with the Al compound and subsequently separated off again before addition to the polymerization system.

As molecular weight regulator and/or to increase the activity, hydrogen is added if required. The total pressure in the polymerization system is from 0.5 to 2500 bar, preferably from 2 to 1500 bar.

The compound of the invention is employed in a concentration, based on the transition metal, of preferably from $10^{-3}$ to $10^{-8}$ mol, preferably from $10^{-4}$ to $10^{-7}$ mol, of transition metal per $dm^3$ of solvent or per $dm^3$ of reactor volume.

Suitable solvents for preparing both the chemical compound of the invention and the catalyst system of the invention are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

Before addition of the catalyst system, in particular the supported catalyst system (comprising at least one chemical compound according to the invention, at least one metallocene, support material and/or a polyolefin powder in finely divided form), another aluminum alkyl compound such as trimethylaluminum, triethylaluminum, triisobutylaluminum, trioctylaluminum or isoprenylaluminum can be additionally introduced into the reactor to make the polymerization system inert (for example for removing catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a low molar Al/M ratio to be selected in the synthesis of a supported catalyst system.

The following examples serve to illustrate the invention.

General procedures: Preparation and handling of organometallic compounds were carried out with exclusion of air and moisture under argon (Schlenk technique). All solvents required were made absolute before use by boiling for a number of hours over suitable desiccants and subsequent distillation under argon.

EXAMPLE 1

1,4-bis(dipentafluorophenylboryl)-2,3,5,6-tetrafluorobenzene 1.54 g (5 mmol) of dibromotetrafluorobenzene are dissolved in 40 ml of n-hexane and cooled to −78° C. 6.4 ml of n-BuLi (10 mmol) are slowly added dropwise to the solution and the mixture is stirred for 1 hour. Subsequently, 1.90 g (5 mmol) of bis(pentafluorophenyl)borylchloride are dissolved in 40 ml of n-hexane and likewise added dropwise to the above solution. The suspension obtained is slowly warmed to room temperature, forming a white precipitant. This is separated off by filtration and the filtrate obtained is evaporated to dryness under reduced pressure. The yield of the resulting 1,4-bis(dipentafluorophenylboryl)-2,3,5,6-tetrafluorobenzene obtained as a yellow oil is 81%.

EXAMPLE 2 bis(dipentafluorophenylboryl)acetylene 1.06 g (5 mmol) of bis(chlorodimethylsilyl)acetylene are dissolved in 40 ml of n-hexane and cooled to −78° C. 1.90 g (5 mmol) of bis(pentafluorophenyl)boryl chloride in 40 ml of n-hexane are slowly added dropwise to this solution. The mixture is stirred for 1 hour at −78° C. and then slowly warmed to room temperature. The solvent and dimethyidichlorosilane formed are removed in a high vacuum. The remaining yellow oil is subsequently fractionally distilled. This gives 2.2 g (61.7% yield) of bis(dipentafluorophenylboryl)acetylene.

EXAMPLE 3

[(dipentafluorophenylboryl)ethynyl]trimethylsilane 1.12 g (5 mmol) of (iodoethynyl)trimethylsilane are dissolved in 40 ml of tetrahydrofuran and cooled to −78° C. 3.2 ml of n-BuLi (5 mmol, 1.6M in hexane) are slowly added dropwise to this solution and the mixture is stirred for 2 hours. Subsequently, 1.90 g (5 mmol) of bis(pentafluorophenyl)boryl chloride are dissolved in 40 ml of tetrahydrofuran and likewise added dropwise to the above solution. The resulting suspension is slowly warmed to room temperature, forming a white precipitate. This is separated off by filtration. The solvent is removed from the filtrate obtained under reduced pressure. The remaining yellow oil is subsequently fractionally distilled. This gives 1.66 g (75% yield) of [(dipentafluorophenylboryl)ethynyl]trimethylsilane.

EXAMPLE 4

[(diphenylphosphino)ethynyl]dipentafluorophenylborane 1.05 g (5 mmol) of diphenyl(ethynyl)phosphine are dissolved in 40 ml of diethyl ether and cooled to −78° C. 3.2 ml of n-BuLi (5 mmol, 1.6M in hexane) are slowly added dropwise to this solution and the mixture is stirred for 2 hours. During this procedure, the solution spontaneously becomes red/brown. Subsequently, 1.90 g (5 mmol) of bis(pentafluorophenyl)boryl chloride are dissolved in 40 ml of tetrahydrofuran and added dropwise to the above solution. The resulting suspension is slowly warmed to room temperature, forming a precipitate. This is separated off by filtration and the filtrate obtained is evaporated to dryness under reduced pressure. The yield of the resulting [(diphenylphosphino)ethynyl]dipentafluorophenylborane obtained as an orange oil is 57%.

EXAMPLE 5 triphenylcarbenium [(dipentafluorophenylborane)-2,3,5,6-tetrafluorophenyl]tripentafluorophenylborate 0.62 g of bromopentafluorobenzene (2.5 mmol) is dissolved in 40 ml of n-hexane and admixed at −78° C. with 1.6 ml of n-BuLi (2.5 mmol, 1.6M in hexane). This suspension is stirred for 1 hour at −10° C. Subsequently, 2.1 g (2.5 mmol) of 1,4-bis(dipentafluorophenylboryl)-2,3,5,6-tetrafluorobenzene in 40 ml of n-hexane are slowly added dropwise to the above solution. The resulting suspension is slowly warmed to room temperature, forming a precipitant. This is separated off by filtration and the filtrate obtained is evaporated to dryness under reduced pressure. The lithium salt thus obtained is taken up in 40 ml of n-pentane and admixed at room temperature with 0.7 g (2.5 mmol) of triphenylmethyl chloride. After stirring for 8 hours, the orange solid is filtered off. The filtrate is extracted with methylene chloride in order to separate off the LiCl formed. Precipitation with n-pentane gives an orange solid (yield: 56%).

EXAMPLE 6

10 g of $SiO_2$ (MS 3030, from PQ, dried at 600° C. in a stream of argon) were suspended in 50 ml of toluene and, while stirring, a solution of 100 mg (0.229 mmol) of dimethylsilanediylbis(2-methylindenyl)dimethylzirconium and 128 mg (0.153 mmol) of 1,4-bis(dipentafluorophenylborane)-2,3,5,6-tetrafluorobenzene in 3 ml of toluene is slowly added dropwise. The mixture is left stirring for 1 hour at room temperature and the solvent is then removed in an oil pump vacuum until the weight is constant. For introduction into the polymerization system, 1 g of the supported catalyst was resuspended in 30 cm³ of Exxsol.

Polymerization:

In parallel thereto, a dry 16 dm$^3$ reactor was flushed first with nitrogen and then with propylene and charged with 10 dm$^3$ of liquid propylene. 0.5 cm$^3$ of a 20% strength triisobutylaluminum solution in Varsol diluted with 30 cm$^3$ of Exxsol were then introduced into the reactor and the mixture was stirred for 15 minutes at 30° C. The catalyst suspension was then introduced into the reactor. The reaction mixture was heated to the polymerization temperature of 60° C. (4° C./min) and the polymerization system was held at 60° C. for 1 hour by cooling. The polymerization was stopped by venting the remaining propylene. The polymer was dried in a vacuum drying oven, giving 1.4 kg of polypropylene powder. The reactor had no deposits on the inner wall or the stirrer. The catalyst activity was 144 kg of PP/g of metallocene×h.

EXAMPLE 7

10 g of SiO$_2$ (MS 3030, from PQ, dried at 600° C. in a stream of argon) are added a little at a time to a solution of 100 mg (0.229 mmol) of dimethylsilanediylbis(2-methylindenyl)dimethylzirconium and 143 mg (0.114 mmol) of triphenylcarbenium [(dipentafluorophenylboryl)-2,3,5,6-tetrafluorophenyl]tripentafluorophenylborate in 50 ml of toluene. The mixture was left stirring for 1 hour at room temperature and the solvent was then removed in an oil pump vacuum until the weight was constant. For introduction into the polymerization system, 1 g of the supported catalyst was resuspended in 30 cm$^3$ of Exxsol.

Polymerization:

In parallel thereto, a dry 16 dm$^3$ reactor was flushed first with nitrogen and then with propylene and charged with 10 dm$^3$ of liquid propylene. 0.5 cm$^3$ of a 20% strength triisobutylaluminum solution in Varsol diluted with 30 cm$^3$ of Exxsol was then introduced into the reactor and the mixture was stirred at 30° C. for 15 minutes. The catalyst suspension was then introduced into the reactor. The reaction mixture was heated to the polymerization temperature of 60° C. (40° C./min) and the polymerization system was held at 60° C. for 1 hour by cooling. The polymerization was stopped by venting the remaining propylene. The polymer was dried in a vacuum drying oven, giving 1.8 kg of polypropylene powder. The reactor had no deposits on the inner wall or the stirrer. The catalyst activity was 186 kg of PP/g of metallocene×h.

What is claimed is:

1. A compound of the formula I

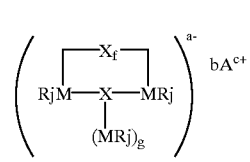

(I)

R are, independently of one another, identical or different and are each a halogen atom, $C_1$–$C_{40}$, haloalkyl, $C_6$–$C_{40}$ haloaryl or $C_7$–$C_{40}$ haloaralkyl group, wherein at least one radical R is a $C_1$–$C_{40}$ haloalkyl, $C_6$–$C_{40}$-haloaryl or a $C_7$–$C_{40}$-haloarlkyle group X are, independently of one another, identical or different and are each a $C_1$–$C_{40}$-haloalkylene, $C_6$–$C_{40}$-arylene, $C_6$–$C_{40}$-haloarylene, $C_7$–$C_{40}$-arylalkylene, $C_7$–$C_{40}$-haloarylalkylene, $C_2$–$C_{40}$-alkynylene, a haloalkynylene group containing up to 40 carbon atoms, $C_2$–$C_{40}$-alkenylene or $C_2$–$C_{40}$-haloalkenylene group, M are, independently of one another, identical or different and are each an element of group IIIa of the Periodic Table of the Elements, a is an integer from 0 to 10, b is an integer from 0 to 10, c is an integer from 0 to 10 and if a=0 then b=0 and if a≧1 then a=b•c, d is 0 or 1, f is 0 or 1, g is 0 or 1, j is an integer from 1 to 2 and A is a cation of group Ia, IIa, IIIa of the Periodic Table of the Elements, a carbenium cation, oxonium cation or sulfonium cation or a quaternary ammonium cation.

2. A compound of the formula I as claimed in claim 1, wherein R are each a halogenated $C_1$–$C_{30}$-alkyl group a halogenated $C_6$–$C_{30}$-aryl group, a, b and c are identical or different and are 0, 1 or 2, j is 3 or 4, and A is a carbenium cation or a quaternary ammonium cation.

3. The compound as claimed in claim 1, wherein X is a $C_6$–$C_{30}$-arylene group, a $C_2$–$C_{30}$-alkenylene group or an alkynylene group with up to 40 carbon atoms, each of which can be halogenated.

4. The compound as claimed in claim 1, wherein M is boron, a, b and c are identical or different and are 0, 1 or 2.

5. A compound of the formula

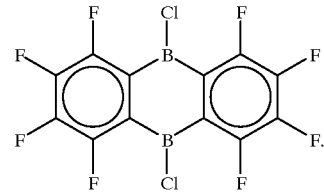

6. The compound as claimed in claim 1, wherein A is carbenium cation or a quaternary ammonium cation having one or more acidic hydrogens.

7. A compound of the formula I

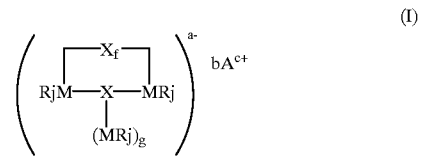

(I)

where

R are, independently of one another, identical or different and are each a halogen atom, $C_1$–$C_{40}$ haloalkyl, $C_6$–$C_{40}$ haloaryl or $C_7$–$C_{40}$ haloaralkyl group, X are, independently of one another, identical or different and are each a $C_2$–$C_{40}$-haloalkylene, $C_6$–$C_{40}$-haloarylene, $C_7$–$C_{40}$-arylalkylene, $C_7$–$C_{40}$-haloarylalkylene or $C_2$–$C_{40}$-alkynylene group or a haloalkynylene group containing up to 40 carbon atoms, M are, independently of one another, identical or different and are each an element of group IIIa of the Periodic Table of the Elements, a is an integer from 0 to 10, b is an integer from 0 to 10, c is an integer from 0 to 10 and if a=0 then b=0 and if a≧1 then a=b•c, f is 0 or 1, g is 0 or 1, j is an integer from 1 or 2

A is a cation of group Ia, IIa, IIIa of the Periodic Table of the Elements, a carbenium cation, oxonium cation, sulfonium cation or a quaternary ammonium cation.

8. The compound as claimed in claim 7, wherein M is boron.

9. The compound as claimed in claim 1, wherein M is boron.

10. A compound selected from the group consisting of

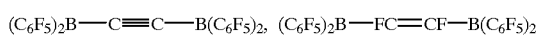

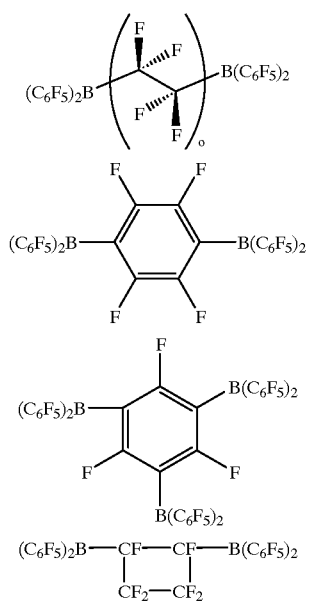

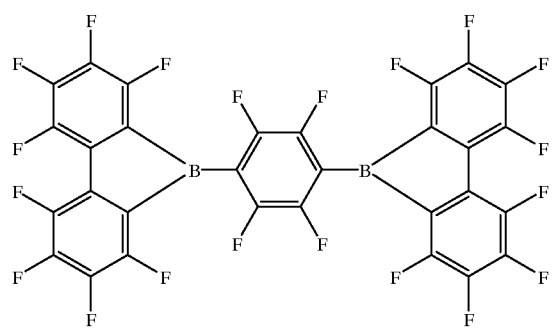

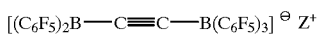

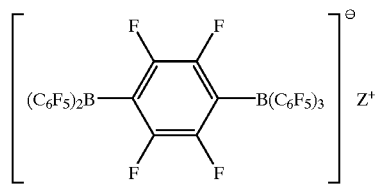

and

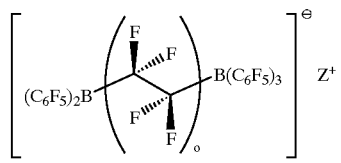

wherein Z is [C₆H₅N(CH₃)₂H] or CPh₃ and o is from 1 to 20.

* * * * *

UNITED STATES PATENT AND TRADEMARK OFFICE
CERTIFICATE OF CORRECTION

PATENT NO.    : 6,255,531 B1                              Page 1 of 1
DATED         : July 3, 2001
INVENTOR(S)   : Fritz et al.

It is certified that error appears in the above-identified patent and that said Letters Patent is hereby corrected as shown below:

<u>Title page,</u>
Item [56], OTHER PUBLICATIONS, CA:121:147733 "phsophorus" should read as -- phosphorus --
CA:130:182880 read "CA:130:182889", it should read as -- CA:130:182880 --

<u>Column 19,</u>
Line 60, "haloarlkyle" should read as -- haloaralkyl --.

<u>Column 20,</u>
Line 49, the formula

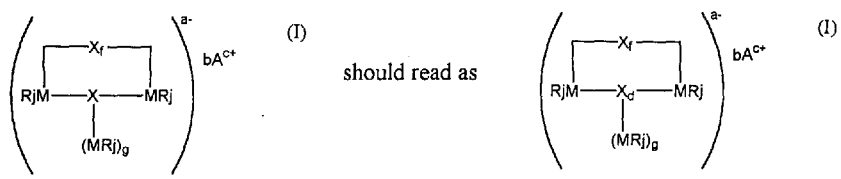

<u>Column 21,</u>
Line 4, "calion" should read -- cation --.

<u>Column 22,</u>
Line 17, "$[(C_6F_5)_2B—FC==CF—B(C_6F_5H)_3]^\ominus Z^+$" should read as
-- $[(C_6F_5)_2B—FC==CF—B(C_6F_5)_3]^\ominus Z^+$ --.

Signed and Sealed this

Twenty-eighth Day of January, 2003

JAMES E. ROGAN
*Director of the United States Patent and Trademark Office*